United States Patent [19]

Lee et al.

[11] Patent Number: 5,494,689
[45] Date of Patent: * Feb. 27, 1996

[54] EDIBLE COMPOSITIONS PROVIDING SALT TASTE-ENHANCING COMPOSITIONS

[75] Inventors: Eldon C. Lee, New Milford; John S. Tandy, Litchfield, both of Conn.

[73] Assignee: Nestec S.A., Vevey, Switzerland

[*] Notice: The portion of the term of this patent subsequent to Jan. 26, 2013, has been disclaimed.

[21] Appl. No.: 349,971

[22] Filed: Dec. 5, 1994

Related U.S. Application Data

[63] Continuation-in-part of Ser. No. 9,325, Jan. 26, 1993, Pat. No. 5,370,882.

[51] Int. Cl.$^6$ .................................................. A23L 1/212
[52] U.S. Cl. ........................... 426/97; 426/649; 426/650
[58] Field of Search .............................. 426/96, 97, 302, 426/649, 650

[56] References Cited

U.S. PATENT DOCUMENTS

| | | |
|---|---|---|
| 2,471,144 | 5/1949 | Davy . |
| 2,601,112 | 6/1952 | Freedman . |
| 3,622,350 | 11/1971 | Hammes . |
| 3,782,974 | 1/1974 | Lontz . |
| 4,068,006 | 1/1978 | Moritz . |
| 4,243,691 | 1/1981 | Mohlenkamp, Jr. et al. . |
| 4,340,614 | 7/1982 | Pich et al. . |
| 4,451,494 | 5/1984 | Roan, III . |
| 4,592,917 | 6/1986 | Tandy . |
| 4,997,672 | 3/1991 | DeSimone et al. . |
| 5,104,672 | 4/1992 | Chen et al. . |
| 5,139,794 | 8/1992 | Patel . |
| 5,370,882 | 12/1994 | Lee . |

*Primary Examiner*—Carolyn Paden
*Attorney, Agent, or Firm*—Vogt & O'Donnell

[57] ABSTRACT

A dehydrated edible composition is provided by a food-acceptable ammonium salt encapsulated in a food-acceptable carrier agent in admixture with at least one of dehydrated meat, vegetable or dairy substance. The encapsulated salt potentiates and enhances the taste of sodium chloride and enables preparation of foods having a reduced sodium chloride content.

20 Claims, No Drawings

EDIBLE COMPOSITIONS PROVIDING SALT TASTE-ENHANCING COMPOSITIONS

CROSS REFERENCE TO RELATED APPLICATION

This application is a continuation-in-part of U.S. patent application Ser. No. 08/009,325, filed Jan. 26, 1993, now U.S. Pat. No. 5,370,882.

BACKGROUND OF THE INVENTION

The present invention relates to salt taste-enhancers more particularly to encapsulated ammonium salts as salt taste-enhancers for food compositions.

Excessive dietary sodium ion intake, the primary source of which is sodium chloride or table salt in foods, has long been associated with a number of health problems such as hypertension. It is generally recognized that the sodium ion intake of most persons is in excess of minimal physiological needs of the body. Consequently, a marked reduction in sodium consumption is recommended for most persons. However, the inclusion of sodium chloride in the diet contributes a good deal to the palatability of foods, and food without salt is perceived to be tasteless, flat and unpalatable.

Heretofore, a number of sodium-free compositions have been suggested as salt substitutes to replace sodium chloride in foods while retaining the palatability of the food. Examples of such salt substitutes are disclosed in U.S. Pat. Nos. 2,471,144; 2,601,112; 3,782,974; 4,243,691; 4,340,614; and 4,451,494.

Among the most popular salt substitutes are potassium chloride, ammonium salts such as ammonium chloride and mixtures thereof. However, such salt substitutes suffer from a number of disadvantages, including off-taste or bitter flavor, a taste perception different from sodium chloride, and a salty impression much less than that of sodium chloride. In particular, ammonium salts are hygroscopic and have a sour aftertaste. Typically, a number of other components must be included to mask a bitterness which the salt substitute, such as potassium or ammonium chloride imparts, such as a combination with potassium chloride of calcium and magnesium formate and citrate salts, sugar, choline citrate and hydrolyzed animal protein.

Another procedure which has been suggested for reducing sodium ion intake is to incorporate salt taste-enhancers in foods and beverages. That is, compounds, which potentiate or amplify the taste of sodium chloride in foods and beverages are incorporated therein so that the sodium chloride content thereof may be reduced without adversely affecting the desired salty taste of the food. For example, U.S. Pat. No. 4,997,672 and the prior art discussed therein disclose the use of substances such as cationic surfactants, bretylium tosylate, certain polypeptides, and the like as salt taste-enhancers.

SUMMARY OF THE INVENTION

We have found that an encapsulated ammonium salt, when added to a food or beverage containing less than a normal amount of sodium chloride, will enhance or potentiate the salty taste of the food or beverage.

Accordingly, the present invention provides a composition enhanced in sodium chloride taste which comprises a food or beverage containing a less than normal amount of sodium chloride and containing a sodium chloride taste-potentiating amount of an encapsulated ammonium salt.

The salt taste-enhancers of the present invention allow the sodium chloride content of a food or beverage to be reduced without adversely affecting the desired salty taste of the product. It is to be understood that the salt taste-enhancers of this invention are not salt substitutes and do not completely replace sodium chloride in the food or beverage. Rather, they are saltiness enhancers and require a minimum level of sodium chloride in the food or beverage of about 0.20% by weight based upon the weight of the food in order to potentiate the sodium chloride taste in the product.

Accordingly, the present invention provides, in addition, a process for potentiating the salty taste of a food or beverage containing a less than a normal amount of sodium chloride by adding to the food or beverage a sodium chloride taste-potentiating amount of an encapsulated ammonium salt.

The present invention also provides a process for preparing a salty tasting food or beverage containing a reduced amount of sodium chloride which comprises formulating a food or beverage with an amount of sodium chloride less than is necessary to achieve a desired salty taste in the food or beverage and potentiating the sodium chloride taste by adding an encapsulated ammonium salt to the food or beverage of reduced sodium chloride content.

The present invention further provides a dehydrated composition of edible substances comprising a food-acceptable ammonium salt encapsulated in a food-acceptable carrier agent which is admixed with at least one of a dehydrated meat, dehydrated vegetable, or dehydrated dairy substance. In this context, the present invention also therefore provides a process for the use of the encapsulated salt wherein the encapsulated salt is admixed with one or more of the stated dehydrated substances.

The dehydrated composition may be reconstituted with water or any with of various liquids containing water, including such as milk. In one embodiment, the composition is suitable and formulated for providing, upon reconstitution, a food intended for consumption alone such as soups, including broths. In other embodiments, the composition is suitable and formulated for providing, upon reconstitution, bouillons for preparing foods or for providing, upon reconstitution, sauces or gravies for the preparation of composite foods, as is known in the food art wherein the sauce or gravy is combined with another food, e.g., vegetable- and meat-based dishes such as potatoes au gratin, or stews, or meat dishes with oriental-type seasonings, or pasta and sauce dishes.

As will be appreciated, therefore, the dehydrated composition of the invention thus may be provided for domestic consumer use in portioned packaged amounts for presenting single or multiple serving portions. The composition also may be formulated advantageously for a commercial industrial setting wherein a mixture of ingredients, including the encapsulated salt, is formulated, with or without sodium chloride, to tailor it for use by manufacturers for admixture with other products for preparation of foods to provide products of reduced sodium content.

In addition, in accordance with the disclosure above, the formulation of the dehydrated composition may be tailored so that the hydrated product has a sodium chloride content of at least about 0.2% by weight based upon the weight of the food or beverage. On the other hand, in other embodiments of the dehydrated composition of the invention, added particulate sodium chloride may be excluded. Therefore, in accordance with the disclosure above, the dehydrated composition is employed for preparing a food or beverage wherein the food or beverage has a sodium chloride content of at least about 0.2% by weight based upon the weight of the food or beverage or may be combined with a food or beverage substance supplying such amount of sodium chloride.

Particularly, when the composition is presented in a packaged portioned amount for making single or multiple servings, the dehydrated composition should contain ammonium chloride in an amount sufficient to enhance the salt taste or perception of the food prepared containing a reduced amount of sodium chloride. When a portioned amount of a composition containing sodium chloride and encapsulated ammonium salt is provided, the sodium chloride and the encapsulated salt may be present in a ratio by weight of ammonium salt to sodium chloride, preferably, of from about 0.25:1 to about 3.75:1 and more preferably from about 0.5:1 to about 2.5:1, which thereby provides a control upon salt usage by such as a domestic consumer.

In addition, in either a commercial industrial or domestic consumer setting, for ease of portioning amounts and incorporation of the product into a food, a bulking agent, i.e., a filler/extender, known in the art, including a starch, particularly such as corn starch, and/or derivatives thereof including dextrins, particularly maltodextrin and cyclodextrin, and the like, for example, may be formulated in the dehydrated composition as a carrier/diluent for the encapsulated salt and other ingredients.

Additionally, the present invention includes a particulate salt taste-enhancer composition comprising particulate sodium chloride in admixture with a food-acceptable ammonium salt encapsulated in a particulate substance comprising a food-acceptable carrier agent. As will be appreciated, such a composition, for example, enables a consumer to salt a food to a desired taste by using less sodium chloride than would be the case if the encapsulated salt were not employed. This composition may be prepared in the weight ratios set forth above and may consist essentially or solely of the sodium chloride and encapsulated salt.

DETAILED DESCRIPTION OF THE INVENTION

Examples of ammonium salts which may be encapsulated are food-acceptable salts such as the chlorides, phosphates, citrates, lactates, tartrates, fumarates, adipates, malates, succinates and gluconates.

One useful source of ammonia which can be converted into an ammonium salt to be encapsulated is ammonia recovered from fermented soy sauce during spray drying, and an especially advantageous source of ammonia is that formed during acidic protein hydrolysis, e.g., ammonia obtained from an evaporator condensate waste stream.

As is known, acid hydrolysis process, animal or plant, e.g., vegetable, or proteins are derived from such as corn, soy, wheat, rice, yeast, peanut, or casein and commonly used starting protein sources may be obtained as a result of the separation of the protein fraction during milling of grains or following solvent extraction of oils. The protein contents of these raw materials may range from 40% to 90%, with a general average of about 60%. Normally, the protein source is hydrolyzed with hydrochloric acid having a concentration of about 20% by weight at a temperature from about 120°–135° C. over a period from about 5 to 8 hours and elevated pressure up to 30 psig (2 bar).

Following hydrolysis, the slurry is neutralized with a suitable alkaline material such as sodium hydroxide or sodium carbonate to a pH of from 5.0 to 5.3, and the residual unhydrolyzed material (lignin, humin) is filtered out. The slurry may be decolorized prior to filtration or the filtrate following filtration may be decolorized by conventional means, e.g., activated carbon, absorption resins.

Following filtration of the unhydrolyzed material and salts formed, the filtered liquid, containing about 42% solids, may be further concentrated to pastes by a vacuum evaporator, and the pastes then are dried in a vacuum oven. Ammonia is removed during vacuum evaporation and may be trapped in the distillate by a condenser forming an evaporator condensate waste stream containing dilute ammonia.

The encapsulated ammonium salt may be obtained from the evaporator condensate waste stream by an evaporator system or by a degassifier system to give a concentrated ammonium salt which may then be spray-dried with the encapsulating agent.

The present invention thus further provides an encapsulated ammonium salt wherein the ammonium salt is derived from ammonia formed during protein hydrolysis.

In the evaporator system, the encapsulated ammonium salt taste-enhancer is prepared by neutralizing the evaporator condensate waste stream with an acid (e.g., hydrochloric acid), concentrating using a vacuum evaporator, purifying with activated carbon, filtering and then spray-drying the filtrate with an encapsulating carrier.

In the degassifier system, the encapsulated ammonium salt taste-enhancer is prepared by heating the evaporator condensate waste stream to a temperature of from 30° C. to just below the boiling point of water, preferably from 35° C. to 96° C. and more preferably from 40° to 90° C., through a heat exchanger, raising the pH to above 9, preferably above 10 and especially 11 with alkali, injecting through a nozzle into a packed tower followed by a forced air degassifier, trapping the volatiles in an acid solution, e.g., concentrated HCl (32%), phosphoric, tartaric, lactic or citric acid to form a salt solution and then, spray-drying the salt solution, containing usually from 15% to 25% by weight solids, with an encapsulating carrier.

Encapsulating agents that may be used include maltodextrin, gum arabic, and gelatinized starches which advantageously are hydrolyzed.

The starches are preferably starches with a high amylopectin content such as waxy cereal starches, e.g., waxy maize starch and waxy rice starch. The starches are conveniently cooked to be gelatinized before hydrolysis and, if desired, they may be modified, preferably at the raw stage. The starches may be hydrolyzed at their 1,6-alpha-D-glycosidic linkages.

The hydrolyzing enzyme may, for instance, be an isoamylase (1,6-alpha-D-glucosidase), a debranching enzyme which specifically hydrolyzes the 1,6-alpha-D-glycoside bonds of branch-chain amylopectin to form amylose without formation of reducing sugars and/or oligosaccharides. Isoamylases may be obtained from broad beans (R-enzyme) or from the fermentation of yeast and bacterial species such as Pseudomonas and Cytophaga. The isoamylase AMANO DB-250 (Amano Enzyme USA Co., Ltd.) is obtained by a fermentation process from a selected strain of *Bacillus sectorramus*.

Other suitable hydrolyzing enzymes include a heat-stable pullulanase debranching enzyme, pullulan 6-glucano-hydrolase, which hydrolyzes the 1,6-alpha-D-glycosidic linkages of amylopectin, and include pullulan, a linear polysaccharide composed of maltotriose units linked by 1,6-alpha-D-glycosidic bonds. The pullulanase AMANO PULLULA-NASE #3 (Amano Enzyme USA Co., Ltd) is obtained by a fermentation process from a selected strain of Aerobacter sp. The pullulanase NOVO PROMOZYME 200L (Novo Nordisk A/S) is obtained from a selected strain of *Bacillus acidopullulyticus* by submerged fermentation and is a U.S. food-grade enzyme, which has been used for preparing a debranching starch hydrolysate for use as the encapsulating agent.

The encapsulated ammonium salt taste-enhancers of the present invention are effective in potentiating or amplifying the salty taste of foods and beverages even when incorporated at relatively low levels. For example, the salty taste of foods and beverages is significantly enhanced by the incorporation therein of encapsulated ammonium salt containing the ammonium salt in an amount of from 0.05 to 0.75%, preferably from 0.1 to 0.5% and especially from 0.15 to 0.3% by weight based on the weight of food or beverage. If the encapsulated ammonium salt contains about 50% by weight of the ammonium salt, then the levels of the encapsulated ammonium salt are from 0.1 to 1.5%, preferably from 0.2 to 1.0% and especially from 0.3 to 0.6% by weight based on the weight of food or beverage.

A salt taste-potentiating amount of encapsulated ammonium salt is effective in potentiating the sodium chloride taste in a wide variety of foods and beverages containing a less than normal amount of sodium chloride, but having a minimum level of sodium chloride of at least about 0.20%. For example, the salty taste of foods such as chicken broth, soups, salad dressing, sauces, mayonnaise, cooked ground beef, oat-meal and the like which are low in sodium, in that they contain a less than normal amount of sodium chloride, is significantly enhanced by the addition of encapsulated ammonium salt in the amounts indicated above. Greater amounts up to about 3% or more of the encapsulated salt may, of course, be used, but preferably, the amount of encapsulated salt used is from 0.1% to 1.5% by weight based on the weight of food or beverage as indicated above.

With regard to the edible dehydrated composition of the present invention referred to above which comprises an encapsulated ammonium salt in admixture with one or more of a dehydrated meat, vegetable or dairy substance, the dehydrated substance(s) may be obtained such as by vacuum-drying, or foam-mat drying, or drum drying, or freeze-drying, including vacuum-freeze-drying, or spray-drying, or other drying processes known in the art. "Dehydrated" is intended to mean that the substance or composition has moisture content such that it is microbiologically stable upon storage at about 21° C. in such as a sealed container package which is substantially impervious to moisture. In particular, the dehydrated substance or composition should be substantially free of free water and/or have a water activity (i.e., a water vapor pressure of the substance or composition compared with the vapor pressure of water measured at the same temperature), of below 0.4, and preferably below 0.3, and more preferably below 0.2. In general, the composition should have a moisture content on the order of less than about 10% by weight based upon the weight of the composition, and preferably less than 7% by weight, and more preferably less than 4% by weight, such being dependent, of course, upon the nature of the composition.

Dehydrated meat, vegetable and dairy substances which may be employed include meats, vegetables and dairy products per se and stocks and extracts derived therefrom such as are used for preparing flavorants and for preparing "instant" foods which are reconstitutible with water as is known in the art. Meats are intended to include animal, fowl and fish meats. Vegetable substances include those commonly employed for foods, including celery, onion, carrot and garlic and extracts thereof and mixtures thereof, for example, and in particular, vegetable substances are intended to include spices and herbs, such as rosemary, thyme, parsley, bay leaf, and basil, etc., and extracts and mixtures thereof. In addition, oleoresins, particularly oleoresin of tumeric, also may be employed. Dairy substances include cheeses prepared by conventional fermentation and/or enzymatic processes and also include milk and whey protein compositions and protein isolates.

Flavorant compositions may be employed advantageously and may be derived from meat and vegetable sources and/or fats and oils thereof. Maillard reaction flavorants are employed usefully, and food-acceptable chemical means, as are known in the art, also may be employed to prepare flavorant agent compositions. The dehydrated composition may also include vitamins, antioxidants and other preservatives and natural and artificial colorants, and any of natural and artificial antioxidants, preservatives and colorants which are food-acceptable may be employed.

In accordance with the disclosure above, the dehydrated composition preferably is formulated (i.e., ingredient usage) and portioned so that upon use of the composition to prepare a food for consumption, the food has from 0.05% to 0.75% and preferably from 0.1% to 0.5% ammonium salt by weight based upon the weight of the food. The dehydrated composition thus may be provided in packaged portions to provide, upon reconstitution, a food such as a soup having these noted use levels. For example, a dehydrated composition of the invention containing the encapsulated ammonium salt may be provided together with instructions for measurement and use, or may be provided in packaged portions, so that the composition is used at a level so that a food containing ammonium salt within the above-noted weight percent ranges is prepared. As will be appreciated, particularly when the dehydrated composition is portion-packaged to achieve reduction of the amounts of sodium chloride employed and consumed, and so that the salt taste-enhancing concept of the presentation is realized, the dehydrated composition is formulated and portioned with sodium chloride so that the food prepared contains sodium chloride in an amount of at least about 0.20% by weight.

The dehydrated composition is prepared readily in particulate form as a mixed blend of ingredients, although such may be formed into a solid mass of a tablet or cube such as a bouillon cube, for ease of portioning, bulking agents, are employed usefully. Acceptable bulking agents include, as noted above, starches, dextrins, particularly, maltodextrins and cyclodextrins, and other food-acceptable substances such as those known and employed in the art as flavorant carriers, or as fillers, or extenders, and such may include flours.

The encapsulated salt may be contained in the composition in a wide range of amounts depending upon, for example, whether the user of the dehydrated composition is an industrial user or a domestic consumer. Particularly, however, when the bulking agent is employed as a carrier, the dehydrated composition generally may contain from about 0.5% to about 10% by weight ammonium salt encapsulated in the food-acceptable carrier agent. In this regard, as will be appreciated, the weight percent of encapsulated salt is dependent upon the amount of agent encapsulating the salt.

Flavorant agent compositions are employed in amounts relative to the intensity of their flavoring effect and the desired ultimate product, and as will be appreciated, such may be associated with carrier agents as are known in the art. In addition to flavorant agents noted above, acid hydrolyzed proteins may be employed for flavoring purposes, but attention should be paid to amounts of sodium contained in such substances so that the objective of reduced sodium content is realized. In general, for many applications, flavorants may be employed in amounts so that the food consumed, including composite foods, contains the flavorant in an amount of from about 0.1% to about 4% by weight.

Vegetable substances also may be employed in the composition of the invention in various amounts, again depending upon the character of the rehydrated product. Spices likewise are employed in amounts desired for a desired seasoning effect and in general, are employed so that the amount of these substances in the food consumed is on the order of from about 0.05% to about 0.5% dry weight based upon the weight of the food.

The dehydrated composition of the invention may be prepared by combining the ingredients in any convenient manner as are known to those skilled in the food flavorant and seasoning art. The individual ingredients may be admixed conveniently in dehydrated form by dry-blending with such as with ribbon blenders manufactured by Charles Ross and Sons (U.S.A.).

Preferably, the dehydrated composition is packaged in a container package, e.g., a sealed envelope or pouch or jar, having printed instructions associated with packaging of the product (i.e., on a portion package or on a box containing portion packs or as an insert) for reconstituting the composition itself as a ready-to-eat product or for combining the dehydrated composition with another component to prepare a composite food product. Conveniently, therefore, the flavorant composition is packaged in a sealed envelope, in an amount sufficient to prepare food portions of predetermined quantity.

EXAMPLES

The following Examples further illustrate the present invention. Parts and percentages are by weight unless otherwise stated.

Example 1

Waxy maize starch (20%) is dispersed in an aqueous solution cooked to 95° C., and then cooled to 40° C. in a Brabender amylograph. Amano pullulanase #3 (Amano Enzyme USA Co., Ltd) (3,000 units/ml) is added at a use level of 0.2% based on the starch. The hydrolysis reaction is carried out with agitation at a constant temperature, 40° C. and viscosity is monitored during reaction.

HPP evaporator condensate (100 kg, ammonium nitrogen 0.210%) is neutralized with 32% hydrochloric acid, concentrated using a vacuum evaporator to 3 kg, purified with activated carbon (100 g Nuchar SA) at 70° C. for 45 min., and then filtered. The filtrate (ammonium nitrogen 5.79%; NH$_4$Cl 22.12%) is mixed with the above starch hydrolysate (2.27 kg), and then spray-dried with an inlet air temperature of 150° C. and outlet temperature of 90° C. to obtain a finished powder product (NH$_4$Cl 48.0%). The recovery yield of ammonium chloride during spray drying is 68.7%. The product is an excellent clean, white powder with low hygroscopicity.

Example 2

Waxy rice starch (20%) is used instead of waxy maize starch as in Example 1, and isoamylase alpha-1,6-D-glucosidase, (AMANO DB-250-Amano Enzyme USA Co., Ltd) (300 units/ml) is used instead of pullulanase at the use level of 2% based on starch. The resulting finished powder product contains 50.0% NH$_4$Cl. The recovery yield of ammonium chloride is 74.0%. The finished product is an excellent clean, white and low hygroscopic powder.

Example 3

A typical low-cost cheese sauce contains approximately 1.6% by wt. sodium chloride. In order to demonstrate the effectiveness of the salt taste-enhancers of the present invention, a comparable low-cost cheese sauce is formulated containing 0.5% sodium chloride and is used as a control. To one aliquot of this control cheese sauce is added 0.40% by weight of the spray-dried encapsulated ammonium chloride (48% NH$_4$Cl by weight) prepared in Example 1. The control cheese sauce and the sauce to which the salt taste-enhancers are added are then evaluated by a sensory panel consisting of eight trained judges who were of the opinion that the salt taste-enhancer significantly amplifies the sodium chloride taste.

Example 4

3.41 g of a low sodium chicken base containing 41 mg Na/g base and 1.69 g of a low sodium beef base containing 83 mg Na/g base are used as test media each in a serving portion of 100 g.

Control samples are made by adding NaCl and KCl to the test media, and a sample according to the present invention is made by adding 0.40 g of the spray-dried encapsulated ammonium chloride (48% NH$_4$Cl by weight) as prepared in Example 1. Each 100 g serving for samples 1, 3 and 4 contains 140 mg sodium each 100 gram serving for sample 2 contains 280 mg sodium. The amounts of NaCl, encapsulated salt, and KCl are given in the following Table 1.

TABLE 1

| Sample | Chicken broth | Beef broth |
| --- | --- | --- |
| 1) Test medium | 3.41 g base | 1.69 g base |
| 2) Control with NaCl added | 3.41 g base +0.36 g NaCl | 1.69 g base +0.36 g NaCl |
| 3) Encapsulated ammonium salt | 3.41 g base +0.40 g | 1.69 g base +0.40 g |
| 4) KCl | 3.41 g base +0.46 g | 1.69 g base +0.46 g |

A sensory panel judges that the encapsulated ammonium salt significantly amplifies the sodium chloride taste. Sample (3) gives comparable salt taste to the control sample (2) and gives better salt taste than the potassium chloride sample (4), which has an undesirable after-taste.

Example 5

About 49.5% of a particulate chicken flavorant composition prepared in accordance with Tandy, U.S. Pat. No. 4,592,917, and spray-dried with a maltodextrin carrier is mixed and blended with about 29.5% maltodextrin to provide further bulk, and with about 5% dry ground rosemary, about 10% dried ground thyme, and about 5% dried oleoresin of tumeric and with about 5% of encapsulated ammonium chloride salt prepared as in Example 1 (48% NH$_4$Cl). The composition so prepared is provided in bulk for use for preparing-chicken flavored food products including, in particular, such as canned or instant soups. The composition is employed in amounts to prepare such foods so that the final food product has sodium chloride amount of at least 0.2% and ammonium chloride amount in the range of from 0.1% to 0.5% as specified above, thus enabling reducing the amount of sodium chloride employed to prepare the product.

Example 6

A mix suitable for preparing beef-flavored gravy is prepared with a beef flavorant composition prepared in accordance with Chen, et al., U.S. Pat. No. 5,104,672, and spray-dried with a maltodextrin carrier. The mix is prepared to contain about 88% of the flavorant composition, about 11% caramel coloring powder, about 0.2% dried ground bay leaf, 0.4% sodium chloride, and about 0.4% encapsulated ammonium chloride salt prepared as in Example 1. The mix is added to water, and flour is mixed in to prepare a gravy.

Example 7

A dehydrated composition for preparation of a chicken noodle soup is prepared with a mix described below which contains dehydrated enriched wheat flour and egg yolk noodles blended therein. The mix contains maltodextrin and corn starch carriers, and dehydrated vegetable, yeast extract, whey, milk and egg yolk powders and a chicken flavorant powder prepared as in Example 5. Sodium chloride and an encapsulated ammonium chloride prepared as in Example 1 (48% NH$_4$Cl) above are included in the mix so that upon addition of water to the composition for consumption, the soup contains about 400 mg sodium per 100 ml/serving and about 0.2% ammonium salt per 100 ml/serving.

Upon hydration and consumption of the soup and upon hydration and consumption of a like soup containing about 800 mg sodium but no encapsulated salt, it is found that the salt-taste perception of each soup is comparable.

As is clear from the foregoing, various modifications of the present invention may be made without departure from the spirit and scope of the disclosure, and the invention may be embodied suitably in the absence of elements, constituent composition components and/or process steps and/or parameters not specifically disclosed or excluded herein.

We claim:

1. A dehydrated composition of edible substances comprising an admixture of (i) a food-acceptable ammonium salt encapsulated in a food-acceptable carrier agent and (ii) at least one substance selected from the group consisting of dehydrated meat, dehydrated vegetable and dehydrated dairy substances.

2. A composition according to claim 1 wherein the carrier agent is selected from the group consisting of maltodextrin, gum arabic and gelatinized starch.

3. A composition according to claim 1 wherein the carrier agent is a gelatinized starch hydrolysate debranched at 1,6-alpha-D-glycosidic linkages.

4. A composition according to claim 1 further comprising particulate sodium chloride.

5. A composition according to claim 4 wherein the ammonium salt and sodium chloride are present in the composition in a ratio by weight of ammonium salt to sodium chloride of from about 0.25:1 to about 3.75:1.

6. A composition according to claim 1 wherein the ratio is from about 0.5:1 to about 2.5:1.

7. A composition according to claim 1 wherein the composition does not contain added particulate sodium chloride.

8. A composition according to claim 1 further comprising a food bulking agent.

9. A composition according to claim 8 wherein the bulking agent is selected from the group consisting of starches, dextrins and flours.

10. A composition according to claim 8 wherein the bulking agent is maltodextrin.

11. A composition according to claim 1 further comprising a food flavorant composition and a spice.

12. A composition according to claim 1 formulated for preparing a soup upon hydration.

13. A composition according to claim 1 formulated for preparing a sauce upon hydration.

14. A composition according to claim 13 formulated for preparing a cheese sauce upon hydration.

15. A composition according to claim 1 formulated for preparing a gravy upon hydration.

16. A particulate salt-taste-enhancer composition comprising particulate sodium chloride in admixture with a particulate substance comprising a food-acceptable ammonium salt encapsulated in a food acceptable carrier agent.

17. A composition according to claim 16 wherein the ammonium salt and sodium chloride are present in the composition in a ratio by weight of ammonium, salt to sodium chloride of from about 0.25:1 to about 3.75:1.

18. A composition according to claim 16 wherein the ammonium salt and sodium chloride are present in the composition in a ratio by weight of ammonium salt to sodium chloride of from about 0.25:1 to about 3.75:1.

19. A composition according to claim 16 wherein the carrier agent is selected from the group consisting of maltodextrin, gum arabic and gelatinized starch.

20. A composition according to claim 16 wherein the carrier agent is a gelatinized starch hydrolysate debranched at 1,6-alpha-D-glycosidic linkages.

* * * * *